United States Patent [19]

Kiesewetter et al.

[11] 4,159,327

[45] Jun. 26, 1979

[54] CEPHALOSPORIN DERIVATIVES, COMPOSITIONS AND METHOD OF USE

[75] Inventors: Erwin Kiesewetter, Stolberg; Heinrich Muckter, Aachen, both of Fed. Rep. of Germany

[73] Assignee: Grünenthal GmbH, Stolberg, Fed. Rep. of Germany

[21] Appl. No.: 859,976

[22] Filed: Dec. 12, 1977

[30] Foreign Application Priority Data

Dec. 10, 1976 [DE] Fed. Rep. of Germany ....... 2655949

[51] Int. Cl.² .................. A61K 31/545; C07D 501/50
[52] U.S. Cl. ...................................... 424/246; 544/26; 544/29
[58] Field of Search ................. 544/26, 29; 424/246

[56] References Cited

U.S. PATENT DOCUMENTS

| | | | |
|---|---|---|---|
| 3,422,100 | 1/1969 | Crast, Jr. | 544/29 X |
| 3,516,997 | 6/1970 | Takano et al. | 544/27 |
| 3,922,268 | 11/1975 | Murphy et al. | 544/16 |
| 3,948,906 | 4/1976 | Eardley et al. | 544/16 |
| 4,042,585 | 8/1977 | Koppel | 544/22 |

FOREIGN PATENT DOCUMENTS

2447194 4/1975 Fed. Rep. of Germany ............. 544/26

OTHER PUBLICATIONS

Raftery, et al. Chemical Abstracts, vol. 65, 4142g (1966).
Kuliev, et al., Chemical Abstracts, vol. 83, 113829j (1975).

*Primary Examiner*—Donald G. Daus
*Assistant Examiner*—Diana G. Rivers
*Attorney, Agent, or Firm*—Weiser, Stapler & Spivak

[57] ABSTRACT

The invention relates to new cephalosporin derivatives, which are effective as antibacterial agents, methods for their production, and medicines containing these products. These compounds have high effectiveness against numerous pathogenic microorganisms, and particularly against gram negative bacilli. Beyond that, the compounds according to the invention are also suitable as intermediate products for the production of further $\beta$-lactam antibiotics.

14 Claims, No Drawings

CEPHALOSPORIN DERIVATIVES, COMPOSITIONS AND METHOD OF USE

DESCRIPTION OF THE INVENTION

The new compounds, which can also exist in the form of pharmaceutically compatible salts, correspond to the formula:

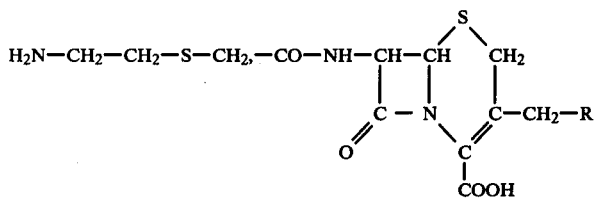

(I)

wherein R is a lower-alkanoyloxy group with up to 5 carbon atoms, particularly the acetoxy group, a 1-methyl- or 1-ethyl-1,2,3,4-tetrazole-5-mercapto radical or a 1,3,4-thiadiazole-2-mercapto radical substituted in position 5 if desired by a lower alkyl radical with 1 to 5 carbon atoms. Preferably, R stands for the 5-methyl-1,3,4-thiadiazole-2-mercapto radical.

The compounds of formula I include acid and amino functions and are therefore capable of formation of corresponding salts with bases or with acids. The production of such salts occurs by a known method which is used to obtain cephalosporin salts.

The compounds of formula I can therefore be produced by reacting a compound of the following formula:

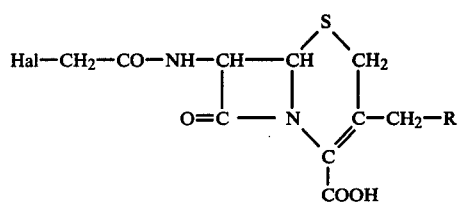

(II)

wherein R has the same meaning as in formula I and Hal stands for a chlorine, bromine or iodine atom, or an easily cleaved ester, particularly a tri-(lower alkyl)silylester of the compound of formula II with 2-aminoethanethiol in the presence of an agent used for binding the resulting hydrogen halogen, preferably a Tri-(lower alkyl)amine. Advantageously, the reaction is carried out in the presence of a solvent in which one of the two reaction products is notably more soluble than the other. Thus the desired cephalosporins of formula I are soluble only with great difficulty in dichlormethane or e.g. chloroform, while e.g. triethylaminehydrochloride is easily soluble in this solvent. Therefore if one of these solvents is used, then the desired product can often be immediately isolated in essentially pure form by simple filtration of the reaction mixture.

On the other hand, the trimethylsilyl esters of the compounds of formula I are easily soluble in solvents such as tetrahydrofuran, dioxane, etc. while e.g. triethylaminehydrochloride is practically insoluble and therefore can be easily removed from a suitable reaction preparation by filtration.

Of course the process can also be carried out in such solvents as water, in which both reaction products are soluble, and from which they are then isolated by suitable subsequent processing (e.g. deposition or extraction of one of the products out of the solution or removal of the solvent from the reaction mixture and extraction of the residue).

The reaction is normally conducted at room temperature, but can be carried out in a temperature range from approximately 0° to 50°.

The compounds of formula I may also be obtained by reacting a compound of formula III:

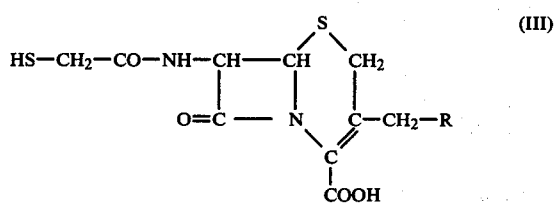

(III)

wherein R is the same as in formula I, with ethylene imine. This reaction preferably occurs in neutral conditions or with the use of solvents such as carbon tetrachloride, etc., and at approximately room temperature up to 60° C.

Finally, such cephalosporins of formula I, in which R is not alkanoyloxy group, can also be obtained by reacting a compound of the formula:

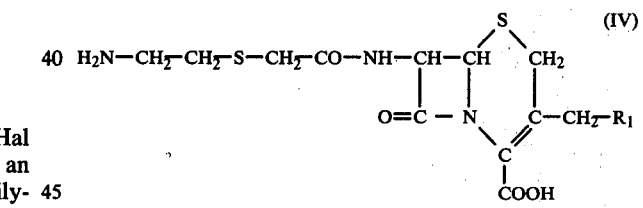

(IV)

wherein $R_1$ is an acetoxy group or a chlorine or bromine atom, with 1-methyl- or 1-ethyl-5-mercapto-1,2,3,4-tetrazol or a 2-mercapto-1,3,4-thiadiazol substituted in position 5 if desired by a lower alkyl radical having 1 to 5 carbon atoms, or with the sodium or potassium salt of such a compound. This reaction occurs at temperatures from 0° to 70° C. in the presence of a solvent, preferably at 40°-60° C. in water.

Further, the object of the invention is medicines, which include at least one of the compounds of formula I, if desired in combination with other substances, in free form or in the form of a salt. Such medicaments, with a compound of the invention, are obtained by preparation of injection solutions or suspensions of certain sterile powders or sterile solutions or suspensions. The compound content of the individual dose is normally 100–5000 mg, preferably 250–4000 mg. For infusions, certain preparation forms could even contain quite large quantities of the materials.

The antibacterial effectiveness of cephalosporins of formula I was proven in animal experiments. Groups of 10 animals were each inoculated with different microorganisms and then the test substances were injected subcutaneously. The value of the $DC_{50}$ (i.e. that dose in mg/kg at which 50% of the animals survive the infection) which was thus determined was set in relation to the $DC_{50}$ value determined by the therapy with cephazolin. The $DC_{50}$ test substance/$DC_{50}$ cephazolin quotient is shown in the following table (the "-" sign means that this test was not carried out):

Test organisms:
A: *Staphylococcus aureus* Smith
B: Penicillinase forming, penicillin resistant staphylococcus-strain
C: *Escherichia coli*
D: *Klebsiella pneumoniae*
E: *Erysipelothrix rhusiopatiae*
F: *Salmonella typhimurium*

| R in the test substance | Test microorganism | | | | | |
|---|---|---|---|---|---|---|
| | A | B | C | D | E | F |
| —OCOCH$_3$ | 2.72 | 0.94 | 3.15 | 1.58 | 0.80 | 2.26 |
| 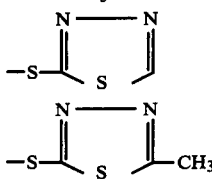 | 0.62 | — | 0.28 | 1.63 | — | — |
| 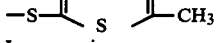 | 0.60 | 0.72 | 0.46 | 0.36 | 0.47 | 0.93 |
| In comparison: Cephazolin | 1.00 | 1.00 | 1.00 | 1.00 | 1.00 | 1.00 |

The following examples serve for further clarification of the invention. All temperatures given therein are uncorrected. Maxiumu yield was not sought to be obtained in carrying out the examples.

The abbreviations used in the examples are the following:

IR: infrared spectrum (determined on molded pieces of KBr)
UV: UV-absorption measured in aqueous solutions (4 mg/10 ml H$_2$O)
NMR: solvent D$_2$O;
  Data in the δ-scale in ppm
  s=singlet, d=doublet, t=triplet, q=quartet, m=multiplet
HPLC: High Performance Liquid Chromatography, with use of a "reverse phase" C$_{18}$-silica gel-support and of the flow agent: water-methanol=2000:400 (+2 ml of a 1% aqueous solution of sodium bicarbonate).
$k_s$: Time from injection until occurrence of the maximum peak in the HPLC.

All analytical data was determined on specimens which were purified by preparatory HPLC and were obtained from the suitable fraction by freeze-drying.

EXAMPLE 1

27 g of 7-aminocephalosporanic acid in 500 ml absolute tetrahydrofuran at room temperature were mixed with slow stirring with 20 ml trimethylchlorosilane and 20 ml triethylamine. After two hours of stirring, a solution of the trimethylsilylester ester of the 7-aminocephalosporanic acid was obtained. After cooling with ice water and addition of 14 ml of triethylamine, 10 ml of bromoacetylbromide were added slowly at 0°–5° C., with stirring. The deposited salts were filtered by suction in the absence of humidity and washed with tetrahydrofuran. The clear, weakly colored filtrate was brought into the water jet vacuum at a bed temperature of up to 30° C. at the highest, for drying. The residue was taken up in 400 ml methylene chloride and was fed, with stirring and at a temperature of 20°–30° C., to a solution of 12 g of 2-aminoethane thiolhydrochloride, 300 ml methylene chloride and 28 ml triethylamine. Upon combining of the solutions, formation of deposits occurred spontaneously. It was stirred for three hours longer without cooling, then the product was filtered by suction and washed with methylene chloride and a little isopropanol. The still moist filter cake was made into a paste in acetone, once again filtered by suction, and then stirred into a mixture of 50 ml methanol and 350 ml isopropanol. After isolation and drying, 35 g of 7-(2'-aminoethylthio)-acetamido-cephalosporanic acid in the form of a pale yellow powder were obtained, which was purified by recrystallization out of aqueous isopropanol.

IR cm$^{-1}$: 3350; 3050-2950; 1770; 1735; 1590.
UV: $\lambda_{max}$=260 nm $E_{1\%}$=225.
$k_s$: 4.0 min.
NMR (ppm): 5.8 (d 1H); 5.3 (d 1H); 3.6 (d 2H) 3.48 (s 2H); 3.2 (m 4H); 2.15 (s 3H).

EXAMPLE 2

0.05 mol of 7-bromoacetamidocephalosporanic acid (obtained as in J. Med. Chem. 16 (1973) 1413-15) were made into a paste in 500 ml methylene chloride and brought into solution by addition of 7 ml of triethylamine at 5°–10° C. The solution was fed into the cooled suspension of 0.05 mol 2-aminoethanethiol in 200 ml methylene chloride with strong stirring. After three hours of stirring, it was filtered by suction and the product washed and further treated as in Example 1.

15.2 g of a powder which had the same features as the 7-(2'-aminoethylthio)-acetamido-cephalosporanic acid described in Example 1 were thus obtained.

EXAMPLE 3

40 ml of a 4% sodium hydroxide solution was trickled with strong stirring and passage of a nitrogen flow at 0° C. into a suspension of 0.02 mol 7-chloracetamidocephalosporanic acid (obtained from 7-aminocephalosporanic acid and chloracetyl chloride as in the process for production of the 7-bromacetamidocephalosporanic acid named in Example 2) and 0.025 mol 2-aminoethanethiolhydrochloride in 100 ml (O$_2$-free) water, so slowly that the pH did not exceed 7.5. Then it was stirred for 2 hours at 0° C. and then for one hour at 20° C. Then the pH value was set at 5.0 by addition of 1 N hydrochloric acid and the water removed by freeze-drying. The residue was triturated with 80% ethanol. The product obtained after drying consisted of the compound named in Example 1. Yield: 6.5.

EXAMPLE 4

17.2 g 7-amino-3-(5'-methyl-1',3',4'-thiadiazol-2'-yl)-thiomethylceph-3-em-4-carboxylic acid (see J. Antib. XXIX (1976) 65, 77) were brought into solution with 15 ml N-methyl-N-trimethylsilyl acetamide in 80 ml tetrahydrofuran. The solution was well stirred and cooled to 0° C. and 7 ml triethylamine were added, and 5 ml bromoacetylbromide slowly added. After 25 minutes, the salts were removed by filtration under a moisture lock, and the tetrahydrofuran was removed by a water jet vacuum. The residue which was thus obtained was taken up in 200 ml methylene chloride and fed into a cooled solution of 6 g of 2-aminoethanethiol-hydrochloride, 14 ml triethylamine and 500 ml methylene chloride. After 3 hours of strong stirring at room temperature, the deposit was filtered by suction, washed, and the still moist filter cake was treated first with 200 ml acetone, then with 200 ml methanol. 16.7 g of 7-(2''-aminoethylthio)-acetamido-3-(5'-methyl-1',3',4'-thiadiazol-2'-yl)-thiomethylceph-3-em-4-carboxylic acid was obtained.

IR cm$^{-1}$: 3350; 3100-3000; 1760; 1670; 1590.
UV: $\lambda_{max}$=275 nm $E_{1\%}$=235.
$k_s$: 12.0 min.
NMR (ppm): 5.8 (d 2H); 5.1 (d 2H); 4.2 (d 2H); 3.5 (s 2H); 3.4 (s 2H); 3.15 (m 4H); 2.8 (s 3H).

EXAMPLE 5

2.65 g of 5-methyl-1,3,4-thiadiazol-2-thiol were dissolved with heat in 50 ml water and 1.4 g of sodium bicarbonate. 7.8 g of the product obtained in example 1 were introduced to this solution and a small quantity of solid material was filtered off. The clear filtrate was heated for 6 hours to 55° C. and then brought into the vacuum to dry. By washing the residue with methanol and acetone, 9.2 g of a powder were obtained after the drying, which amounted to 65% (determined by HPLC) of the product described in example 4.

EXAMPLE 6

2.4 g of 1,3,4-thiadiazol-2-thiol were heated in 25 ml water with 1.5 g sodium bicarbonate, and the solution obtained thereby of the sodium salt of the thiol was combined with the solution of 7.8 g of 7-(2'-aminoethylthio)-acetamidocephalosporanic acid in 100 ml H$_2$O. After heating, the solution was held for 15 hours at 55° C. The reaction solution was treated with 5 g of the adsorber resin found in commerce under the name "Servachrom XAD Type 2" (particle size 100-200μ), and after filtration, brought into the vacuum for drying. The residue was triturated with 200 ml methanol and dried.

The 7-(2''-aminoethylthio)-acetamido-3-(1',3',4'-thiadiazol-2'-yl)-thiomethyl-ceph-3-em-4-carboxylic acid yield was 7.8 g.

IR cm$^{-1}$: 3350; 3050-2950; 1790; 1660; 1590;
$\lambda_{max}$=270 nm $E_{1\%}$=265.
$k_s$: 9.5 min.
NMR (ppm): 9.75 (s 1H); 5.75 (d 1H); 5.2 (d 1H); 4.25 (d 2H); 3.7 (d 2H); 3.48 (s 2H); 3.1 (m 4H).

EXAMPLE 7

9 g of 7-amino-3-(1'-methyl-1'H-tetrazol-5'-yl)-thiomethylceph-3-em-carboxylic acid (see J. Antib. XXIX (1976) 65, 77) were dissolved in 100 ml of tetrahydrofuran by addition of 20 ml of N-methyl-N-trimethylsilyl acetamide, and then treated at 0°-5° C. with 3.5 ml triethylamine and subsequently with 2.5 ml of bromoacetyl-bromide. The reaction mixture was filtered under a moisture lock, and then freed from tetrahydrofuran in the vacuum. The residue was absorbed in 200 ml methylene chloride and brought to reaction with a solution of 3 g of 2-aminoethanethiol-hydrochloride, 300 ml methylene chloride and 7 ml triethylamine at 20°-25° C. After isolation, washing and drying, analogous to the process described in example 4, 7 g of 7-(2''aminoethylthio)-acetamido-3-(1'-methyl-1'H-tetrazol-5'-yl)-thiomethyl-ceph-3-em-4-carboxylic acid was obtained.

IR cm$^{-1}$: 3350; 2100-3000; 1760; 1670; 1590.
$\lambda_{max}$=270 nm $E_{1\%}$=245.
$k_s$: 6.5 min.
NMR (ppm): 5.6 (d 1H); 5.2 (d 1H); 4.2 (d 1H); 4.1 (s 3H); 3.7 (d 2H); 3.48 (s 2H); 3.2 (m 4H).

EXAMPLE 8

As in the process described in example 5, 7-(2'-aminoethylthio)-acetaminocephalosporanic acid in the presence of sodium bicarbonate was reacted with 1-methyl-1,2,3,4-tetrazol-5-thiol and 9.5 g of a product was obtained in which 55% of the cephalosporin produced in example 7 could be detected by HPLC.

We claim:

1. 7-(2''-aminoethylthio)-acetamido-3-(5'-methyl-1',3',4'-thiadiaxol-2'-yl)-thiomethyl-ceph-3-em-4-carboxylic acid of the following formula

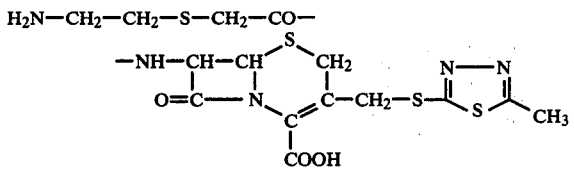

and its salts with pharmaceutically acceptable bases or acids.

2. An antibacterial pharmaceutical composition which comprises a pharmaceutically acceptable carrier and, in a therapeutically and antibacterially effective amount, the carboxylic acid or its salt with a pharmaceutically acceptable base or acid of claim 1.

3. A method of controlling bacteria which comprises administering the composition of claim 2 to a subject in an amount sufficient to control bacteria.

4. The method of controlling bacteria of claim 3 wherein the amount is from about 100 to 5000 mg.

5. The method of controlling bacteria of claim 4 wherein the amount is from about 200 to 4000 mg.

6. The method of controlling bacteria of claim 3 wherein the bacteria is gram-negative bacteria.

7. The carboxylic acid of claim 1.

8. The salt of the carboxylic acid of claim 1 with a pharmaceutically acceptable base.

9. The salt of the carboxylic acid of claim 1 with a pharmaceutically acceptable acid.

10. An antibacterial pharmaceutical composition which comprises a pharmaceutically acceptable carrier and, in a therapeutically and antibacterially effective amount, the carboxylic acid of claim 1.

11. An antibacterial pharmaceutical composition which comprisea a pharmaceutically acceptable carrier and, in a therapeutically and antibacterially effective amount, the salt of the carboxylic acid of claim 1 with a pharmaceutically acceptable base.

12. An antibacterial pharmaceutical composition which comprises a pharmaceutically acceptable carrier and, in a therapeutically and antibacterially effective amount, the salt of the carboxylic acid of claim 1 with a pharmaceutically acceptable acid.

13. The composition of claim 2, wherein said composition is an injectable solution.

14. The method of controlling bacteria of claim 3, wherein said bacteria are selected from the group consisting of Staphylococcus aureus Smith, Penicillinase forming, penicillin resistant staphylococcus-strain, Escherichia coli, Klebsiella pheumoniae, Erysipelothrix rhusiopatiae or Salmonella typhimurium.